United States Patent [19]

Rounbehler et al.

[11] 4,277,259
[45] Jul. 7, 1981

[54] AIR-SAMPLING CARTRIDGE

[75] Inventors: David P. Rounbehler, Concord; Robert S. Potts, Sherborn, both of Mass.

[73] Assignee: Thermo Electron Corporation, Waltham, Mass.

[21] Appl. No.: 120,401

[22] Filed: Feb. 11, 1980

[51] Int. Cl.³ ............... G01N 31/06; B01D 47/00; B01D 53/30
[52] U.S. Cl. ....................... 55/270; 55/356; 55/350; 55/387; 23/232 R; 220/379; 422/88
[58] Field of Search ............... 55/270, 485, 482, 480, 55/503, 505, 350, 356, 387; 422/61, 88, 102, 104, 103; 23/232 R; 73/23, 23.1; D19/43; 220/379

[56] References Cited

U.S. PATENT DOCUMENTS

| | | | |
|---|---|---|---|
| 2,283,989 | 5/1942 | Henry | 55/503 |
| 3,681,899 | 8/1972 | Grote | 55/503 |
| 3,941,573 | 3/1976 | Chapel | 55/316 |
| 3,966,410 | 6/1976 | Jahnsen | 23/230 B |
| 3,992,153 | 11/1976 | Ferber et al. | 422/88 |
| 4,003,257 | 1/1977 | Fletcher et al. | 73/23.1 |
| 4,123,932 | 11/1978 | Baker et al. | 73/28 |
| 4,178,794 | 12/1979 | Jugle et al. | 55/270 |
| 4,194,884 | 3/1980 | Rounbehler et al. | 422/88 |

FOREIGN PATENT DOCUMENTS 227721  6/1963  Austria ........................ 55/503

OTHER PUBLICATIONS

Zip-Mark Corp., P.O. Box 4006, Jersey City, N. J., 1965, one page.

Primary Examiner—William F. Smith
Assistant Examiner—Chris Konkol
Attorney, Agent, or Firm—Herbert E. Messenger; James L. Neal

[57] ABSTRACT

An air-sampling cartridge is disclosed for collecting organic compounds such as N-nitrosamines from air for analysis. The cartridge is formed by joining two injection-molded plastic parts: a generally cylindrical cartridge body into which air-pervious packings of granular adsorbent materials may be loaded, and a cartridge cap which is ultrasonically welded to the body to partially close one end of the cartridge. The cap and body define a cartridge with an inlet and outlet shaped to facilitate connection of the cartridge to a pump used to draw air samples through the cartridge, to allow connection of two or more cartridges in series, and to accommodate standard-sized syringes used in removing trapped compounds from the cartridge for analysis.

The cartridge also includes a retention clip integrally molded with the cartridge body and cap for permitting the cartridge to be attached to the clothing of a person during air-sampling. Also provided are two shipping caps which are held within storage wells on the cartridge body during air-sampling and which at other times are used to seal the inlet and outlet of the cartridge to prevent contamination of the adsorbent material and compounds trapped therein.

4 Claims, 6 Drawing Figures

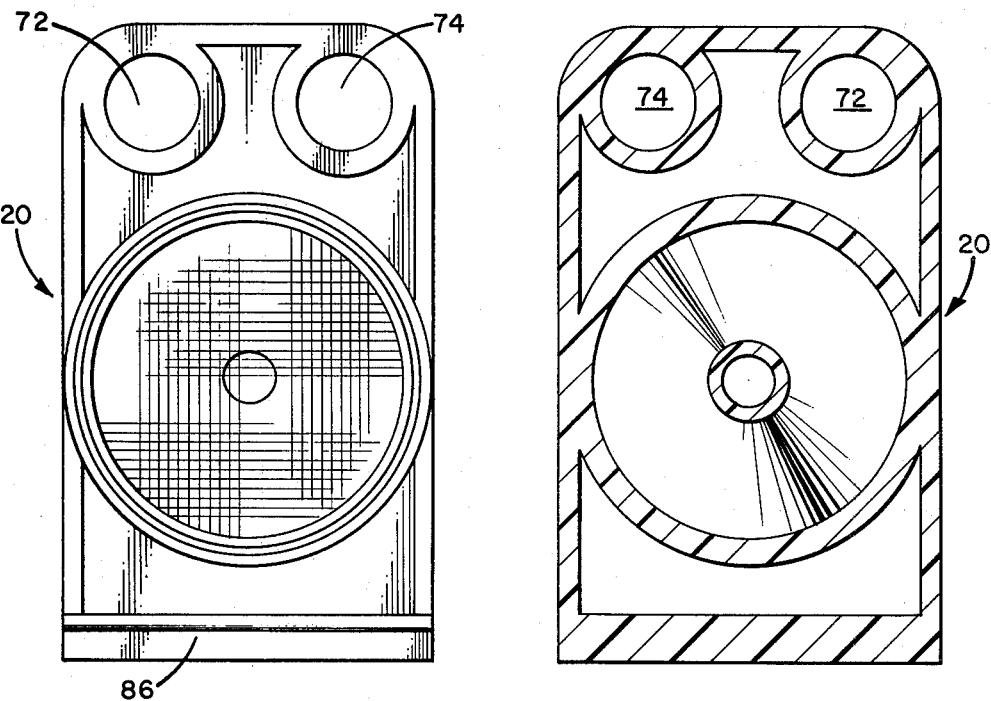
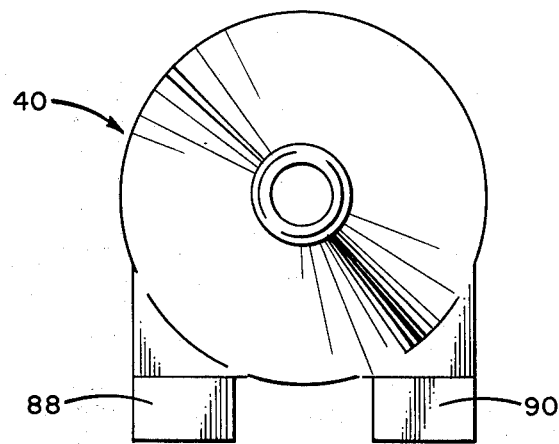

AIR-SAMPLING CARTRIDGE

CROSS REFERENCE TO RELATED APPLICATIONS

This application is related to U.S. Patent Application Ser. No. 963,626 entitled "Method and Apparatus For Air Sampling and Filtration", filed Nov. 24, 1978, issued Mar. 25, 1980 as U.S. Pat. No. 4,194,884, and to U.S. Patent Application Ser. No. 061,554, entitled "Method and Apparatus For Extraction of Airborne N-Nitroso Compounds Without Artifact Formation", filed July 27, 1979. The disclosures of those applications are incorporated by reference herein.

BACKGROUND OF THE INVENTION

This invention relates to air-sampling apparatus. In particular, it concerns cartridges for carrying packings of adsorbent material and for collecting compounds such as N-nitrosamines from air for subsequent analysis.

The suspected presence in air of certain organic compounds which are harmful to animals, and may be harmful to people, makes it desirable to monitor the air in certain locations to identify specific compounds and determine their concentrations. One class of organic compounds of particular interest are N-nitrosamines or N-Nitroso compounds, which have the general formula

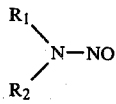

where $R_1$ and $R_2$ are the same or different organic radicals. Several of these N-Nitroso compounds are known to be highly carcinogenic to animals and may be similarly harmful to people. Hence the recent discovery of certain airborne N-nitrosamines in factories and at other sites is cause for concern regarding exposure of workers to these compounds, and indicates that monitoring of such personnel and sites may be needed.

One known apparatus for collecting organic compounds such as N-nitrosamines from a sample of air is a trap which contains a liquid solution of potassium hydroxide through which an air sample is bubbled. Such "bubble traps", however, suffer from poor collection efficiency for certain compounds of interest, are too cumbersome for use as a personnel monitor, and yield a sample extract which is difficult and time-consuming to analyze.

Another collection device, described in U.S. Pat. No. 4,003,257 to Fletcher et al, comprises a glass test tube-like body open at one end and tapering to a small opening at the other end. The body is packed with an adsorbent material sold under the trademark TENAX-GC, which is held in place by glass wool at each end of the packing. These glass tubes are resistant to the moderately high temperatures used in subsequent desorption of the trapped volatile organic compounds, but may break during handling. The glass tubes also require a separate container for storage or transport, and lack features permitting their attachment to and use by a person in monitoring his breathing atmosphere.

Accordingly, it is an object of the invention to provide apparatus for carrying an adsorbent material, and particularly apparatus which in combination with the adsorbent material carried therein, is an improved air-sampling device.

It is an object of the invention to provide an air-sampling cartridge which may be readily attached to the clothing of a person and used to monitor air to which the person is exposed.

It is also an object of the invention to provide a disposable air-sampling cartridge which is easy to make and load with adsorbent material, and is convenient and safe to use in the collection of organic compounds.

It is a particular object of the invention to provide an air-sampling cartridge which facilitates accurate collection and analysis of air samples containing N-Nitroso compounds.

SUMMARY OF THE INVENTION

The invention concerns apparatus for carrying an air-pervious packing of granular adsorbent material and which is particularly effective in combination with the packing in the collection of organic compounds from a sample of air. The apparatus is a cartridge formed by joining a cartridge body to a cartridge cap, preferably by ultrasonically welding these two parts after a packing of granular adsorbent material has been loaded into the cartridge body. The cartridge cap and body, which are preferably injection-molded plastic parts, together define a cartridge with an elongated inlet and an elongated outlet which allow air samples to be readily directed through the cartridge for trapping of selected compounds such as N-nitrosamines and which also facilitate passage of solvents through the cartridge for elution of the trapped compounds.

In a preferred embodiment of the invention two shipping caps are included with the cartridge for sealing its inlet and outlet at times such as during shipment of the cartridge, thereby preventing contamination of the adsorbent material and compounds trapped therein. Cylindrical wells are provided in an exterior portion of the cartridge body for storing these shipping caps during air sampling. Also included is a retention clip formed by a web integral with the cartridge body and by clips projecting from the cartridge cap. The retention clip permits the attachment of the cartridge to the clothing of a person or to any other thin object during air-sampling.

BRIEF DESCRIPTION OF THE DRAWINGS

FIG. 4 is an end view in cross-section of the cartridge body taken along the line 4—4 of FIG. 3.

FIG. 5 is a top view of a cartridge body according to a preferred embodiment of the invention.

FIG. 6 is a top view of a cartridge cap according to a preferred embodiment of the invention.

DETAILED DESCRIPTION OF A PREFERRED EMBODIMENT

According to a preferred embodiment of the invention, a two-part, generally cylindrical container is provided for carrying a granular adsorbent material. The novel container, when packed with the adsorbent material, forms an air-sampling device which is very effective in collecting N-nitrosamines and other organic compounds for later analysis. It is particularly useful as a monitor which may be attached to the clothing of a person and operated to trap N-nitrosamines in air drawn through the container.

Figure 1:
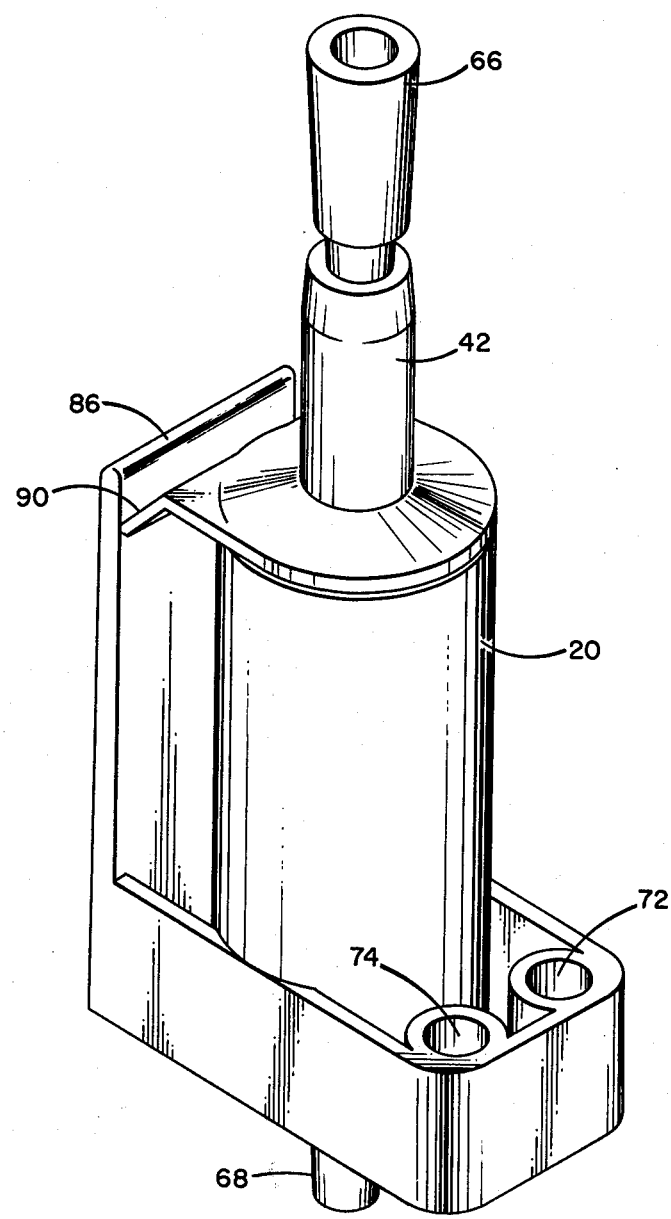
FIG. 1 is a view in perspective of an air-sampling cartridge according to a preferred embodiment of the invention, and showing shipping caps positioned in the inlet and outlet of the cartridge.
Figure 2:
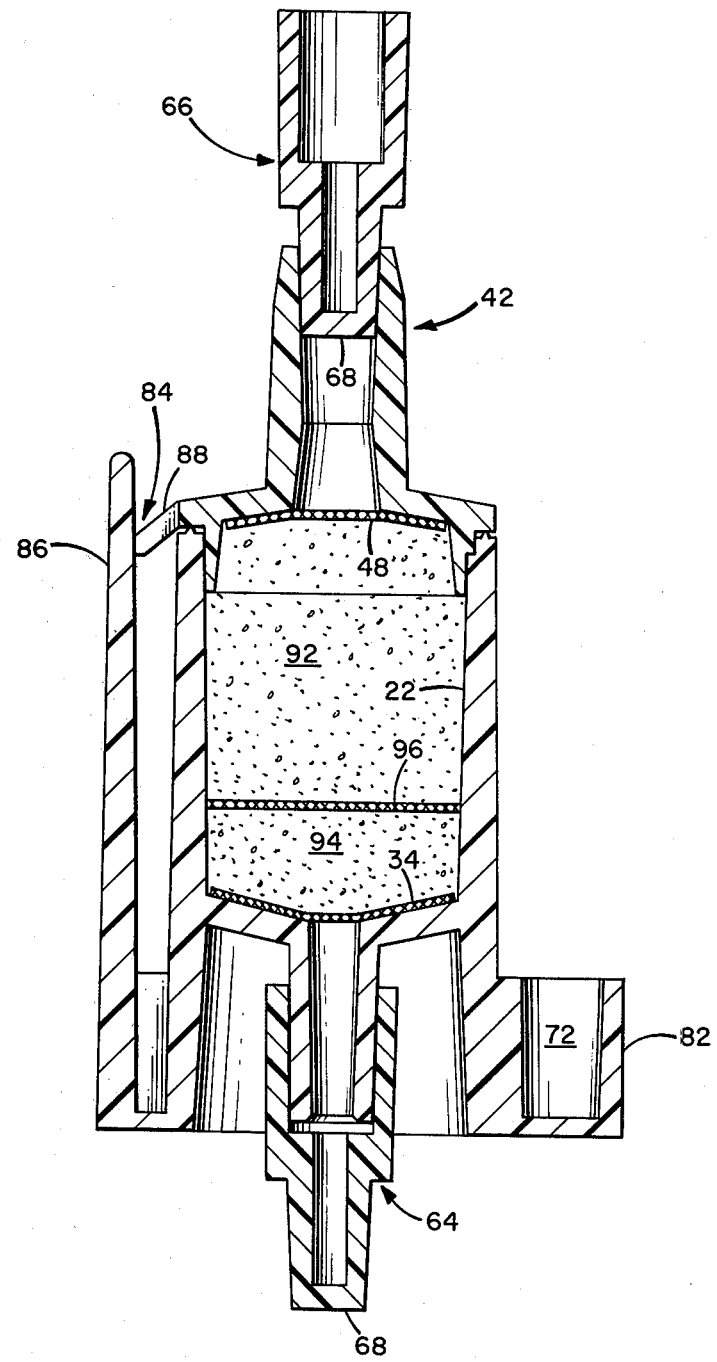
FIG. 2 is a side view in cross-section of the preferred air-sampling cartridge of FIG. 1 as assembled for transport and carrying a packing of a granular adsorbent material.
Figure 3:
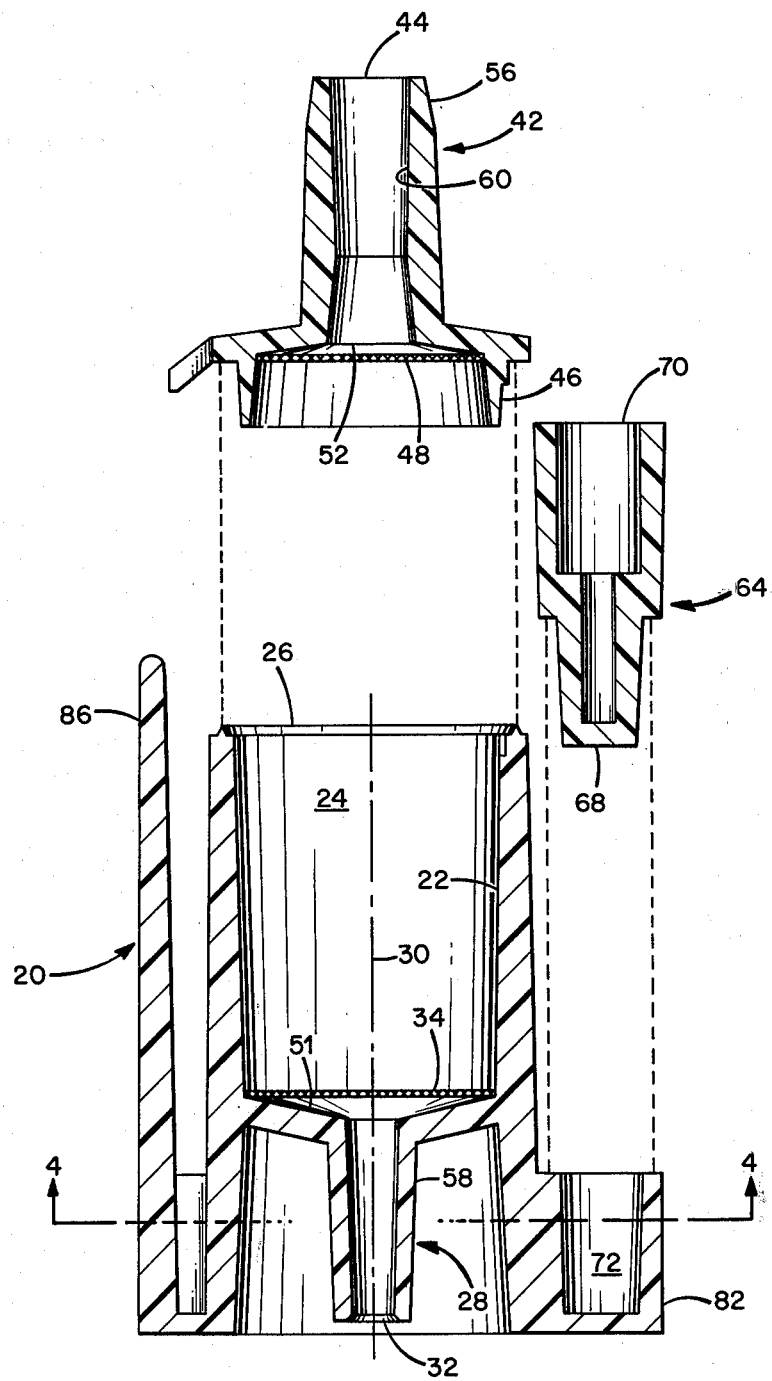
FIG. 3 is an exploded side view in cross-section of the cartridge showing its two major components, and also showing one of the two shipping caps provided with the cartridge.

In FIGS. 1-5 there is shown a cartridge body 20 which constitutes a primary component of the apparatus disclosed and claimed herein. The cartridge body 20, whose inner structure is clearly evident in FIG. 3, is preferably formed as an integral piece by injecting molding of a suitable plastic material such as nylon. A thin cylindrical wall 22 of the body 20 defines a cavity 24 into which packings such as granular adsorbent materials may easily be loaded through an open end 26 of the body 20. The opposite end of the cartridge body 20 includes an elongated outlet 28 extending along an axis 30 of the body and terminating in an outlet port 32. The port 32 is preferably of substantially smaller diameter than the diameter of the open end 26 and is in fluid communication with the cavity 24. To prevent passage of adsorbent material from the cavity 24 through the outlet 28 during loading and air-sampling, a porous retainer 34 such as a stainless steel screen is positioned in the cavity 24 prior to loading of adsorbent material into the cartridge body 20.

FIGS. 6 and 3 show top and side views, respectively, of a cartridge cap 40 suitable for attachment to the cartridge body 20 to form a closed container or cartridge (see FIG. 2). The cap 40 preferably is formed by injection molding of plastic material. One suitable material for the cap 40 and the body 20 is Zytel 101-gray 48, a nylon material manufactured by E. I. Dupont de Nemours and Company of Wilmington, Del. This material, in addition to being readily moldable, is stable against outgassing, thus avoiding contamination of the compounds collected within the cartridge during sampling. Also, this material is opaque, thus avoiding alteration of light-sensitive compounds such as N-nitrosamines collected therein.

As is shown in FIG. 3, the cap includes an elongated inlet 42 at one end thereof which terminates in an inlet port 44. At its opposite end, the cap 40 has a flange 46 which is sized to fit tightly to the open end 26 of the cartridge body 20 by contacting the end, and a portion of the inner surface, of the wall 22. Prior to placement of the cap 40 and the body 20 in close proximity, a porous retainer 48 similar to the retainer 34 is positioned within the cap 40 and one or more packings of granular adsorbent material are loaded into the cavity 24 through the open end 26 of the body 20. A rigid container or cartridge (FIGS. 1 and 2) comprising the cartridge cap 40 and the cartridge body 20 may then be obtained by ultrasonically welding the flange 46 of the cap 40 to the wall 22 of the body 20. The retainers 48 and 34 thereafter prevent passage of granular adsorbent material and any other packings through the inlet 42 and the outlet 28 of the thus-formed container.

As is apparent from FIGS. 2 and 3, the retainers 34 and 48 may be flexible and deform under pressure of the packings loaded into the cavity 24 to conform to the end surfaces 51 and 52 of the body 20 and of the cap 40 respectively, thus assuring that the retainers and packings remain tightly held within the cartridge.

The inlet 42 and the outlet 28 of the cartridge formed by joining of the body 20 and the cap 40 have surfaces shaped to facilitate several aspects of air-sampling. As is shown in FIG. 3, the outer surface 56 of the inlet 42 is shaped such that it may be held within one end of a hose whose opposite end is connected to an air pump (not shown) for drawing air through the cartridge during sampling. The outer surface 58 of the outlet 28 is sized to closely fit within the inner surface 60 of the inlet 42 of an identical cartridge. This allows two or more cartridges to be deployed in series during air-sampling for checking the "breakthrough" capacity of a single cartridge—i.e. its capacity for trapping and retaining all of the N-nitrosamines or other selected compounds in the air sample passed therethrough.

Also, the surfaces 60 and 58 readily interface with, respectively, standard male and female syringe fittings which may be used during removal of trapped compounds from the cartridge for analysis.

To seal the inlet and outlet ports 44 and 32 during shipment of the cartridge and thus assure no contamination of its contents, two identical shipping caps 64 and 66 are provided. Each shipping cap such as the cap 64 shown in FIG. 3 is preferably molded of rubber or plastic and includes a solid end 68 shaped to closely fit within the inner surface 60 of the inlet 42 and an open end 70 shaped to closely fit around the outer surface 58 of the outlet 28. Thus each cap may be used to seal either the inlet port 44 or the outlet port 32. FIG. 2 shows an assembled cartridge with the shipping caps 64 and 66 connected thereto and blocking the inlet port 44 of the cartridge cap 40 and the outlet port 32 of the cartridge body 20.

To permit storage of the shipping caps—e.g., during use of the cartridge for air-sampling, two wells 72 and 74 are formed in an enlarged solid portion 82 of the cartridge body 20 radially outward of the outlet 28. Each well is shaped to tightly retain a cap such as the cap 64 by its solid end 68 as is indicated in FIG. 3.

Use of the cartridge as a personnel monitor is facilitated by a retention clip 84 formed in part by a generally flat, flexible web 86 having one end integrally molded with the cartridge body 20 and the remainder extending along the cartridge body 20 generally parallel to and spaced from the wall 22 thereof. One or more clips such as the clips 88 and 90 (FIG. 6) project from the cartridge cap 40 an amount such that when the cap 40 and the body 20 are joined the clips 88 and 90 are located close to or in contact with the web 86 (see FIGS. 1 and 2). The retention clip 84 formed by the web 86 and the clips 88 and 90 readily permits entry of a thin material such as the shirt collar of a wearer but inhibits its removal without flexing the web 86 away from the clips 88 and 90.

The web 86, in addition to forming part of the retention clip 84, also provides a flat outside surface which facilitates labelling of the cartridge with data such as the sampling date and location and the name of the user of the cartridge.

FIG. 2 shows a cartridge assembled for transport either prior to or following air-sampling and containing a packing 92 of an adsorbent material particularly suited for collection of airborne N-nitroso compounds such as N-nitroso-dimethylamine, -morpholine-pyrrolidine, -diethylamine, and others. In one arrangement of packings shown and described in the above-referenced U.S. Application Ser. No. 061,554, the packing 92 is a mixture of about 5 percent of a solid-phase granular amine complexing agent such as sulfamic acid and about 95 percent of a granular sorbent such as magnesium silicate. A second packing 94 of a solid-phase, granular amine complexing agent such as sulfamic acid is also provided between the retainer and a porous separator 96. The packing 94 acts to trap amines present in an air sample directed through the cartridge so that no artifact formation of N-nitrosamines may occur from precursors in the sample as is explained in greater detail hereinafter. The separator 96, which may be a stainless steel screen similar to the retainers 34 and 48, serves to prevent intermixing of the packings 92 and 94 within the cartridge.

Fabrication of the cartridge of the invention and its use with packings of adsorbent materials as an air-sampler will now be reviewed. First the cartridge body 20, the cartridge cap 40, and the shipping caps 64 and 66 are injection-molded as four separate pieces. The cartridge body 20 is placed on a flat surface with its open end 26 oriented vertically upward and a porous retainer 34, preferably a stainless steel screen, is placed in the bottom of the cavity 24 adjacent to the outlet 28. Next a packing 94 of a granular amine complexing agent such as granular sulfamic acid of 30-80 mesh size is loaded into the cavity 24 and is covered by a stainless steel screen or other separator 96. Another packing 92 comprising a mixture of a particulate sorbent such as granular magnesium silicate of 30-80 mesh size (95 percent by volume) and an amine complexing agent such as granular sulfamic acid of 30-80 mesh size (5 percent by volume) is then added to fill the cavity 24. The cartridge top 40, into which a stainless steel screen 48 has been inserted, is fitted to the open end 26 of the cartridge body 20 as shown in FIG. 2 then the top 40 and the body 20 are ultrasonically welded at the joint therebetween to form a sealed container or cartridge. The shipping caps 64 and 66 are then placed in position blocking the inlet port 44 and the outlet port 32 of the cartridge to prevent contamination of the packings 92 and 94 during storage and shipment of the cartridge.

To monitor a particular environment such as the air to which a person is exposed for the presence of N-nitroso compounds, the shipping caps 74 and 66 are removed from the cartridge and stored in the wells 72 and 74, and the cartridge is connected to an air pump (not shown) by attaching the free end of a hose leading from the pump to the inlet 42 of the cartridge cap 40. If the cartridge is to be worn as part of a personnel monitor, it is attached by means of the retention clip 84 to a shirt collar or elsewhere on the clothing of the person whose environment is to be sampled. In such applications the cartridge may typically be about 1½ inches in length and have a maximum width of about 1 inch, and the air pump utilized may be a small battery-operated pump which can be carried within a pocket or on the belt of the person being monitored.

After the pump and the cartridge are connected, the pump is started and operates for a preselected period of time to draw a known volume of air into the cartridge through the outlet port 32 of the cartridge body 20 and then successively through the outlet 28 and the packings 94 and 92, and then out through the inlet 42 of the cartridge cap 40. The packing 94 traps substantially all the amines in the air sample and the packing 92 traps substantially all of the N-Nitroso compounds and at least a portion of the nitrogen oxides present in the air sample.

After sampling is completed, the pump is stopped and its hose disconnected from the inlet 42. The clip 84 is unclipped from the person monitored, and the shipping caps 74 and 66 may be reattached to the inlet 42 and the outlet 28 for shipment of the cartridge to a lab for analysis of the trapped compounds. Preferably the analysis includes backflushing the cartridge with a small amount of an elutent such as acetone to remove any N-nitroso compounds trapped in the packing 92. The elutent, which preferably is injected into the cartridge by means of a syringe inserted into the inlet 42 thereof, dissolves both the N-nitroso compounds trapped in the packing 92 and the amine complexing agent of the packing 92. The amine complexing agent in turn reacts with the nitrogen oxides trapped in the packing 92 to render the oxides of nitrogen unable to support N-nitrosation. As the solution of elutent and materials carried therein then passes into and through the packing 94, the oxides of nitrogen are not available to participate with the amines trapped in the packing 94 in an N-nitrosation reaction. Thus there can be substantially no artifact formation of N-nitroso compounds in the cartridge 50, and the solution collected after emergence from the outlet port 32 contains the N-nitroso compounds originally present in the air sample and no other N-nitroso compounds.

After selected compounds such as the N-nitroso compounds are eluted from the packings 92 and 94 and collected, the collected solution is analyzed according to known techniques. One preferred method comprises injecting a portion of the solution into a chromatograph to separate the N-nitroso compounds from each other and from any nitrates or nitrites which are present, then non-catalytically pyrolyzing the chromatograph effluent at a temperature in the range 300° C.-500° C. to selectively break the N-NO bond in the N-nitroso compounds and release gaseous nitric oxide. The amount of nitric oxide liberated, which is a direct indication of the concentration of N-Nitroso compounds, may then be measured as by reacting the nitric oxide with ozone and sensing the intensity of the resulting chemiluminescent reaction.

Accordingly, there has been shown and described a cartridge for carrying packings of adsorbent material and which in combination with the packings forms an air sampler for trapping compounds such as N-nitrosamines. The cartridge is easy to fabricate and assemble, and is particularly adaptable for use as part of an air-sampler which may be worn by a person.

While the invention has been shown and described with respect to a preferred embodiment thereof, it is apparent that the air-sampling cartridge may be embodied in other specific forms without departing from the spirit or essential characteristics of the invention. The scope of the invention is indicated by the appended claims, and all changes which come within the range of equivalency of these claims are intended to be embraced therein.

What is claimed is:

1. Apparatus for carrying an air-pervious packing of adsorbent material, and useful in combination therewith for collecting compounds from an air sample, comprising:

a cartridge body including a thin, nearly cylindrical wall defining a cavity for receiving a packing of adsorbent material, said body having a first end open for admitting said packing and a hollow elongated outlet opposite said first end and having an outlet port therein;

a cartridge cap having a hollow elongated inlet at one end thereof with an inlet port therein, said cap being sealably attachable to the first end of said cartridge body to form a cartridge;

said inlet having an inner surface of a shape similar to the outer surface of said outlet to permit series connection of said cartridge to a second cartridge identical thereto by insertion of the outlet of one of said cartridges into the inlet of the other of said cartridges;

retainer means in said cartridge body and said cartridge cap for, upon receipt of adsorbent material in said cavity, preventing the passage of adsorbent material through the outlet of said body and, after attachment of said cartridge cap to the body, through the inlet of said cap, said retainer means being porous to the flow of air and selected solvents therethrough; and a pair of shipping caps removably attachable to said inlet and said outlet for blocking the inlet port and outlet port at selected times, said caps being storable in a pair of wells formed in said cartridge body outside said nearly cylindrical wall;

said outlet having an outer diameter appreciably smaller than the outer diameter of said inlet to avoid inadvertent connection of said outlet to a pump for air sampling.

2. Apparatus as in claim 1 wherein said cartridge body includes a flexible web extending along at least a portion of said cartridge body and having one end thereof rigidly attached to said body, said web having a flat, outwardly facing surface suitable for recording information thereon;

said cartridge cap including at least one clip projecting therefrom;

said clip and said web arranged to be positioned in close proximity to each other upon attachment of said cartridge cap to said body, and operable to permit entry therebetween of a thin object and to inhibit removal of said object without flexure of said web away from said clip.

3. Apparatus as in claim 1 wherein said cartridge cap and said body are formed by injection molding of an opaque nylon material stable against outgassing.

4. Apparatus as in claim 1 wherein said shipping caps are substantially identical and each of said shipping caps comprises a peg having a first end shaped for insertion into, and tight retention by, the inlet of said cartridge cap and a second end shaped to receive and tightly retain the outlet of said cartridge body.

* * * * *